(12) United States Patent
Humphrey

(10) Patent No.: US 8,267,973 B2
(45) Date of Patent: Sep. 18, 2012

(54) FIXABLE SUTURE ANCHOR PLATE AND METHOD FOR TENDON-TO-BONE REPAIR

(75) Inventor: Scott Humphrey, Boise, ID (US)

(73) Assignee: Shoulder Options, Inc., Boise, ID (US)

( * ) Notice: Subject to any disclaimer, the term of this patent is extended or adjusted under 35 U.S.C. 154(b) by 989 days.

(21) Appl. No.: 12/038,577

(22) Filed: Feb. 27, 2008

(65) Prior Publication Data

US 2009/0216270 A1 Aug. 27, 2009

(51) Int. Cl.
*A61F 2/30* (2006.01)
(52) U.S. Cl. .......... 606/280; 606/902; 606/232
(58) Field of Classification Search ........... 606/232, 606/280–286, 289, 69, 86 B, 144, 148, 589, 606/902–906, 915; 623/13.12, 20.14, 20.32, 623/20.35
See application file for complete search history.

(56) References Cited

U.S. PATENT DOCUMENTS

| | | | |
|---|---|---|---|
| 5,201,768 A * | 4/1993 | Caspari et al. | 623/20.32 |
| 5,776,199 A * | 7/1998 | Michelson | 623/17.16 |
| 6,093,201 A * | 7/2000 | Cooper et al. | 606/232 |
| 6,344,042 B1 | 2/2002 | Curtis et al. | |
| 6,383,186 B1 * | 5/2002 | Michelson | 606/70 |
| 6,428,577 B1 * | 8/2002 | Evans et al. | 623/20.29 |
| 6,491,714 B1 | 12/2002 | Bennett | |
| 6,508,830 B2 * | 1/2003 | Steiner | 606/232 |
| 6,514,274 B1 * | 2/2003 | Boucher et al. | 606/232 |
| 6,554,852 B1 | 4/2003 | Oberlander | |
| 6,712,830 B2 | 3/2004 | Esplin | |
| 6,719,759 B2 | 4/2004 | Wagner et al. | |
| 6,821,278 B2 | 11/2004 | Frigg et al. | |
| 6,830,572 B2 | 12/2004 | McDevitt et al. | |
| 7,001,388 B2 | 2/2006 | Orbay et al. | |
| 7,090,676 B2 | 8/2006 | Huebner et al. | |
| 7,179,260 B2 | 2/2007 | Gerlach et al. | |
| 7,294,130 B2 | 11/2007 | Orbay | |
| 7,303,577 B1 | 12/2007 | Dean | |
| 7,621,914 B2 * | 11/2009 | Ralph et al. | 606/71 |
| 7,780,710 B2 * | 8/2010 | Orbay et al. | 606/286 |

(Continued)

OTHER PUBLICATIONS

Christopher D. Smith, et al.; A Biomechanical Comparison of Single and Double-Row Fixation in Arthroscopic Rotator Cuff Repair; J Bone Joint Surg Am. 2006; 88:2425-2431. doi:10.2106/JBJS.E.00697; (8 pages).

(Continued)

*Primary Examiner* — Corrine M McDermott
*Assistant Examiner* — Mark Mashack
(74) *Attorney, Agent, or Firm* — Holland Law Office PLLC

(57) ABSTRACT

A fixable suture anchor plate including an anchor plate having a tunnel aperture that aligns with one or more bone tunnels formed in the bone. The anchor plate also includes one or more suture passages that align with one or more grooves formed along an edge of the anchor plate to permit passing a suture through the anchor plate after the anchor plate is fixed to the bone. The anchor plate also includes a screw hole that allows the anchor plate to be fixed to a bone with a screw. A method for tendon-to-bone repair includes sewing a medial row of stitches proximate to a medial line of tendon-to-bone attachment and securing the suture to the anchor plate through a bone tunnel and sewing a lateral row of stitches along a lateral line of tendon-to-bone attachment and securing the second suture to the anchor plate.

8 Claims, 7 Drawing Sheets

U.S. PATENT DOCUMENTS

| | | | |
|---|---|---|---|
| 2001/0051815 A1 | 12/2001 | Esplin | |
| 2003/0100901 A1* | 5/2003 | Wellisz et al. | 606/72 |
| 2003/0135213 A1* | 7/2003 | LeHuec et al. | 606/69 |
| 2004/0049194 A1* | 3/2004 | Harvie et al. | 606/72 |
| 2004/0167522 A1 | 8/2004 | Niederberger et al. | |
| 2004/0254609 A1 | 12/2004 | Esplin | |
| 2005/0010226 A1* | 1/2005 | Grady et al. | 606/69 |
| 2005/0070904 A1 | 3/2005 | Gerlach et al. | |
| 2005/0165395 A1* | 7/2005 | Orbay et al. | 606/60 |
| 2005/0182405 A1* | 8/2005 | Orbay et al. | 606/69 |
| 2006/0149265 A1 | 7/2006 | James et al. | |
| 2006/0173458 A1* | 8/2006 | Forstein et al. | 606/69 |
| 2006/0212035 A1* | 9/2006 | Wotton, III | 606/69 |
| 2006/0264946 A1 | 11/2006 | Young | |
| 2006/0276896 A1* | 12/2006 | Fallin et al. | 623/16.11 |
| 2007/0093835 A1 | 4/2007 | Orbay et al. | |
| 2007/0142836 A1 | 6/2007 | Schmieding et al. | |
| 2007/0270853 A1 | 11/2007 | Leung | |
| 2008/0177313 A1* | 7/2008 | Lemoine et al. | 606/250 |
| 2010/0042102 A1* | 2/2010 | Hamel | 606/54 |

OTHER PUBLICATIONS

Maria Apreleva, Ph.D., et al.; Rotator Cuff Tears: The Effect of the Reconstruction Method on Three-Dimensional Repair Site Area; 2001 Richard O'Connor Award Paper; Arthroscopy: The Journal of Arthroscopic and Related Surgery, vol. 18, No. 5 (May-Jun.), 2002: pp. 519-526; (8 pages).

Pol E. Huijsmans, et al.; Arthroscopic Rotator Cuff Repair with Double-Row Fixation; J Bone Joint Surg Am. 2007;89:1248-1257. doi:10.2106/JBJS.E.00743 (11 pages).

Julie Bishop, MD, et al.; Cuff integrity after arthroscopic versus open rotator cuff repair: A prospective study; J Shoulder Elbow Surg 2006;15:290-299; (10 pages).

Pascal Boileau, et al.; Arthroscopic Repair of Full-Thickness Tears of the Supraspinatus: Does the Tendon Really Heal?; J Bone Joint Surg Am. 2005;87:1229-1240. doi:10.2106/JBJS.D.02035; (13 pages).

Stephen S. Burkhart, M.D., et al.; Cyclic Loading of Transosseous Rotator Cuff Repairs Tension Overload as a Possible Cause of Failure; Arthroscopy: The Journal of Arthroscopic and Related Surgery, vol. 13, No. 2 (Apr.), 1997: pp. 172-176; (5 pages).

Stephen S. Burkhart, M.D., et al.; Cyclic Loading of Anchor-Based Rotator Cuff Repairs "Confirmation of the Tension Overload Phenomenon and Comparison of Suture Anchor Fixation With Transosseous Fixation; Arthroscopy." The Journal of Arthroscopic and Related Surgery, vol. 13, No. 6 (Dec.). 1997: pp. 720-724; (5 pages).

Joseph P. Burns, MD, et al.; Arthroscopic rotator cuff repair in patients younger than 50 years of age; J Shoulder Elbow Surg 2007 :1-7.

Edwin R. Cadet, MD, et al.; The relationship between greater tuberosity osteopenia and the chronicity of rotator cuff tears; J Shoulder Elbow Surg 2007; :1-5.

George L. Caldwell, Jr., M.D. et al.; Strength of Fixation with Transosseous Sutures in Rotator Cuff Repair; Journal of Bone and Joint Surgery—American 1996-1998; Jul. 1997, vol. 79-A, No. 7; 1064-8; (5 pages).

P. T. Calvert, et al.; Arthography of the Shoulder After Operative Repair of the Torn Rotator Cuff; 1986 British Editorial Society of Bone and Joint Surgery 030I-620X/86/ 1052; Vol. 68-B, No. I.; 147-150; (4 pages).

Craig A. Cummins, MD, et al.; Mode of failure for rotator cuff repair with suture anchors identified at revision surgery; Journal of Shoulder and Elbow Surgery 058-2746/2003; vol. 12.; No. 2; 128-133; (6 pages).

COL Thomas M. DeBerardino, MD, et al.; All-Inside Arthroscopic Repair of Partial-Thickness Supraspinatus Tendon Tear; Techniques in Shoulder and Elbow Surgery 8(3):117-119, 2007; (3 pages).

Michael J. DeFranco, MD, et al.; Functional outcome of arthroscopic rotator cuff repairs: A correlation of anatomic and clinical results; J Shoulder Elbow Surg 2007;16:759-765; (7 pages).

Allen Deutsch, MD; Arthroscopic Rotator Cuff Repair: The Effect of Depth of Suture Passage on Three-Dimentional Repair Site Surface Area and Load to Failure Using Single-Row Anchor Fixation; 2006 American Shoulder and Elbow Surgeons Open Meeting; Chicago, IL, USA; Mar. 25, 2006; e41; (1 page).

Stephen Fealy, M.D., et al.; Mini-Open Rotator Cuff Repair Using a Two-Row Fixation Technique: Outcomes Analysis in Patients With Small, Moderate, and Large Rotator Cuff Tears; Arthroscopy: The Journal of Arthroscopic and Related Surgery, vol. 18, No. 6 (Jul.-Aug.), 2002: pp. 665-670; (6 pages).

Leesa M. Galatz, et al.; The Outcome and Repair Integrity of Completely Arthroscopically Repaired Large and Massive Rotator Cuff Tears; J Bone Joint Surg Am. 2004;86:219-224; (7 pages).

DT Harryman, et al.; Repairs of the rotator cuff. Correlation of functional results with integrity of the cuff; J Bone Joint Surg Am. 1991;73:982-989; (9 pages).

T. Kenneth Kaar, M.D., et al.; Complications of Metallic Suture Anchors in Shoulder Surgery: A Report of 8 Cases; Arthroscopy: The Journal of Arthroscopic and Related Surgery, vol. 17, No. 1 (Jan.), 2001: pp. 31-37; (7 pages).

Laurent Lafosse, M.D., et al.; Footprint Fixation for Arthroscopic Reconstruction in Anterior Shoulder Instability: The Cassiopeia Double-row Technique; Arthroscopy: The Journal of Arthroscopic and Related Surgery, vol. 22, No. 2 (Feb.), 2006: pp. 231.e1-231.e6; (6 pages).

Edward Lee, MD, et al.; Outcomes after arthroscopic rotator cuff repairs; J Shoulder Elbow Surg 2007;16:1-5; (5 pages).

Stephen H. Liu, M.D., et al.; Arthroscopically Assisted Rotator Cuff Repair: Correlation of Functional Results with Integrity of the Cuff; Arthroscopy: The Journal of Arthroscopic and Related Surgery 10(1):54-60; (7 pages).

Ian K. Y. Lo, M.D., et al.; Double-Row Arthroscopic Rotator Cuff Repair: Re-Establishing the Footprint of the Rotator Cuff; Arthroscopy: The Journal of Arthroscopic and Related Surgery, vol. 19, No. 9 (Nov.), 2003: pp. 1035-1042; (8 pages).

C. Benjamin Ma, et al.; Biomechanical Evaluation of Arthroscopic Rotator Cuff Stitches; J Bone Joint Surg Am. 2004;86:1211-1216; (7 pages).

C. Benjamin Ma, et al.; Biomechanical Evaluation of Arthroscopic Rotator Cuff Repairs: Double-Row Compared with Single-Row Fixation; J Bone Joint Surg Am. 2006;88:403-410; (9 pages).

Andrew T. Mahar, MS, et al.; Increasing the insertion depth of suture anchors for rotator cuff repair does not improve biomechanical stability; J Shoulder Elbow Surg 2005;14: 626-630; (5 pages).

Steven W. Meier, MD, et al.; Rotator cuff repair: The effect of double-row fixation on three-dimensional repair site; (J Shoulder Elbow Surg 2006;15:691-696; (6 pages).

George S. Athwal, et al.; Osteolysis and Arthropathy of the Shoulder After Use of Bioabsorbable Knotless Suture Anchors. A Report of Four Cases; J Bone Joint Surg Am. 2006;88:1840-1845; (7 pages).

Laurent Lafosse, et al.; The Outcome and Structural Integrity of Arthroscopic Rotator Cuff Repair with Use of the Double-Row Suture Anchor Technique; J Bone Joint Surg Am. 2007;89:1533-1541; (10 pages).

Mehmet Ozbaydar, M.D., et al.; The Use of Anchors in Shoulder Surgery: A Shift From Metallic to Bioabsorbable Anchors; Arthroscopy: The Journal of Arthroscopic and Related Surgery, vol. 23, No. 10 (Oct.), 2007: pp. 1124-1126; (3 pages).

Maxwell C. Park, MD, et al.; Part I: Footprint contact characteristics for a transosseous-equivalent rotator cuff repair technique compared with a double-row repair technique; J Shoulder Elbow Surg 2007;16:461-468; (8 pages).

Maxwell C. Park, MD, et al.; Part II: Biomechanical assessment for a footprint-restoring transosseous-equivalent rotator cuff repair technique compared with a double-row repair technique; J Shoulder Elbow Surg 2007;16:469-476; (8 pages).

Hiroyuki Sugaya, et al.; Repair Integrity and Functional Outcome After Arthroscopic Double-Row Rotator Cuff Repair. A Prospective Outcome Study; J Bone Joint Surg Am. 2007;89:953-960; (9 pages).

Alberto G. Schneeberger, et al.; Mechanical Strength of Arthroscopic Rotator Cuff Repair Techniques: An in Vitro Study; (10 pages).

Marc D. Silver, M.D., et al.; Symptomatic Interarticular Migration of Glenoid Suture Anchors; Arthroscopy: The Journal of Arthroscopic and Related Surgery, vol. 16, No. 1 (Jan.-Feb.), 2000: pp. 102-105; (4 pages).

P St Pierre, et al.; Tendon-healing to cortical bone compared with healing to a cancellous trough. A biomechanical and histological evaluation in goats; J Bone Joint Surg Am. 1995;77:1858-1866; (10 pages).

L. Sward, et al.; The Strength of Surgical Repairs of the Rotator Cuff; J Bone Joint Surg [Br] 1992 ; 74-B :585-8; (4 pages).

Shane J. Nho, et al.; Systematic Review of Arthroscopic Rotator Cuff Repair and Mini-Open Rotator Cuff Repair; J Bone Joint Surg Am. 2007;89:127-136; (11 pages).

Markus J. Tingart,; Pullout Strength of Suture Anchors Used in Rotator Cuff Repair; J Bone Joint Surg Am. 2003;85:2190-2198; (10 pages).

Stephen C. Weber, MD, et al.; Distant migration of a bioabsorbable implant in the shoulder; J Shoulder Elbow Surg 2006;15:e48-e53; (6 pages).

Ken Yamaguchi, et al.; Transitioning to Arthroscopic Rotator Cuff Repair: The Pros and Cons; J Bone Joint Surg Am. 2003;85:144-155; (13 pages).

Thomas Youm, MD, et al.; Arthroscopic versus mini-open rotator cuff repair: A comparison of clinical outcomes and patient satisfaction; J Shoulder Elbow Surg 2005;14: 455-459; (5 pages).

JD Zuckerman, et al.; Complications about the glenohumeral joint related to the use of screws and staples; J Bone Joint Surg Am. 1984;66:175-180; (7 pages).

Arthrex, Inc. and Ernst Wiedemann; Brochure—The Arthrex Humeral SuturePlate, Proximal Humeral Fracture Management System; Copyright Arthrex Inc., 2006, (16 pages).

Arthrex, Inc.; Brochure—The Next Generation in Shoulder Repair Technology; Copyright Arthrex Inc., 2007; (23 pages).

Synthes (USA); K011815—Synthes LCP Proximal Humerus Plate; FDA listed device; Sep. 6, 2001; (4 pages).

Acumed LLC; K071715—Acumed Congruent Bone Plate System; FDA listed device; Jul. 18, 2007; (4 pages).

Biomet Inc.; K991009—Biomet RC Buttress; FDA listed device; Jun. 23, 1999; (4 pages).

EBI, L.P.; K062494—EBI OptiLock Upper Extremity Plating System; FDA listed device; Oct. 19, 2006; (4 pages).

Arthroteck, Inc.; K033838—Titanium Toggle Button(s); FDA listed device; Feb. 13, 2004; (4 pages).

Zimmer, Inc.; K042695—NCB Plating System; FDA listed device; Oct. 29, 2004; (5 pages).

DePay Mitek; K052630—Rotator Cuff Quick Anchor Plus; FDA listed device; Oct. 17, 2005; (5 pages).

Arthrex, Inc.; K031666—Arthrex ACL RetroReconstruction Button Kit; FDA listed device; Nov. 18, 2003; (4 pages).

Arthrex, Inc.; K062747—Arthrex RetroButton; FDA listed device; Sep. 29, 2006; (4 pages).

Arthrex, Inc.; K010673—Arthrex FiberWIRE; FDA listed device; May 14, 2001; (4 pages).

Arthrex, Inc.; K012923—Arthrex FiberWIRE USP size 5 suture; FDA listed device; Oct. 4, 2001; (4 pages).

Arthrex, Inc.; K021434—Arthrex FiberWIRE USP suture family; FDA listed device; Nov. 7, 2002; (4 pages).

DePuy, Inc.; K031969—DePuy Restore Orthobiological Soft Tissue Implant; FDA listed device; Jul. 28, 2003; (5 pages).

Lifecell Corp.; K071986—LTM-RC Surgical Mesh; FDA listed device; Jul. 20, 2007; (1 page).

ITS Implantat-Technologie-Systeme GmbH; K051412—Humeral Head Plate with Angular Stability; FDA listed device; Jul. 11, 2005; (4 pages).

Tornier; K060545—Unity Humeral Plate; FDA listed device; Apr. 21, 2006; (5 pages).

Synthes (USA); K994364—Synthes Button Plate; FDA listed device; Mar. 15, 2000; (4 pages).

Smith & Nephew, Inc.; K980155—EndoButton Continuous Loop; FDA listed device; Apr. 1, 1998; (6 pages).

Arthrex, Inc.; K052776—TightRope Acrromicroclavicular; FDA listed device; Dec. 13, 2005; (5 pages).

ConMed Linvatec; K070780—Conmed Linvatec XO Button—Titanium Fixation Device; FDA listed device; Aug. 21, 2007; (7 pages).

Amon T. Ferry, MD, et al.; Double-Row Rotator Cuff Repairs: Biomechanical Rationale and Surgical Techniques; Techniques in Shoulder & Elbow Surgery 9(1):1-9, 2008; (9 pages).

* cited by examiner

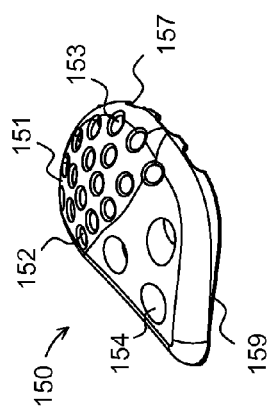
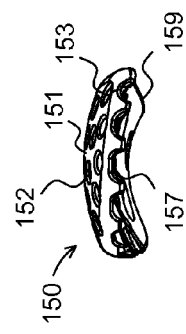
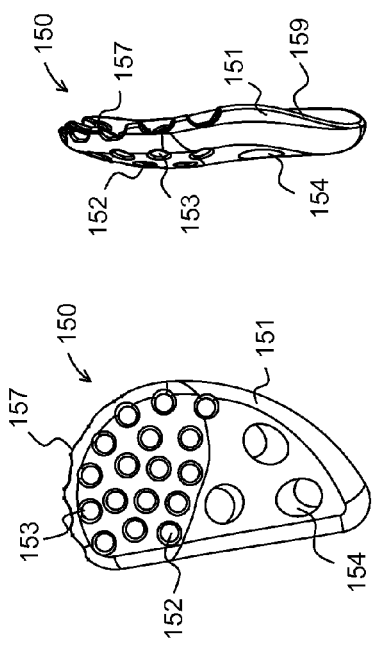
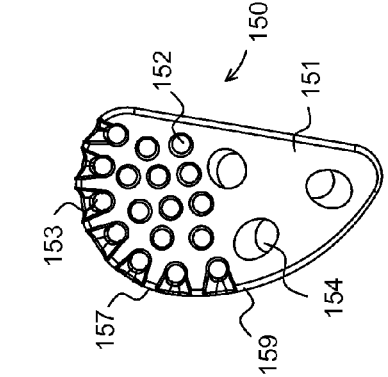
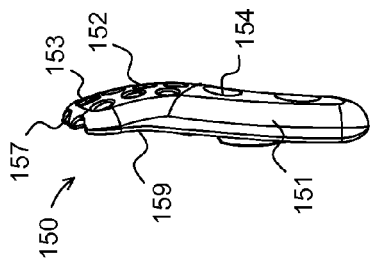
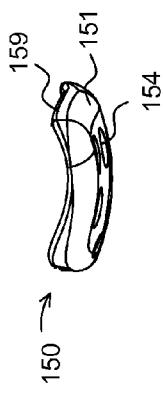
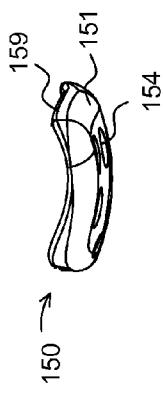

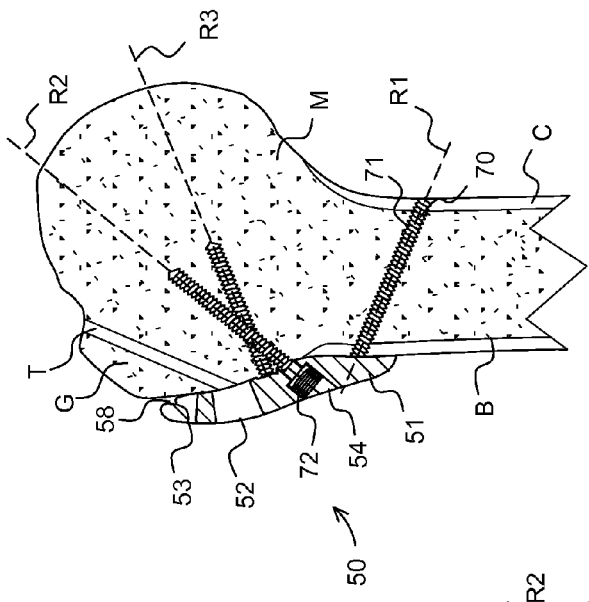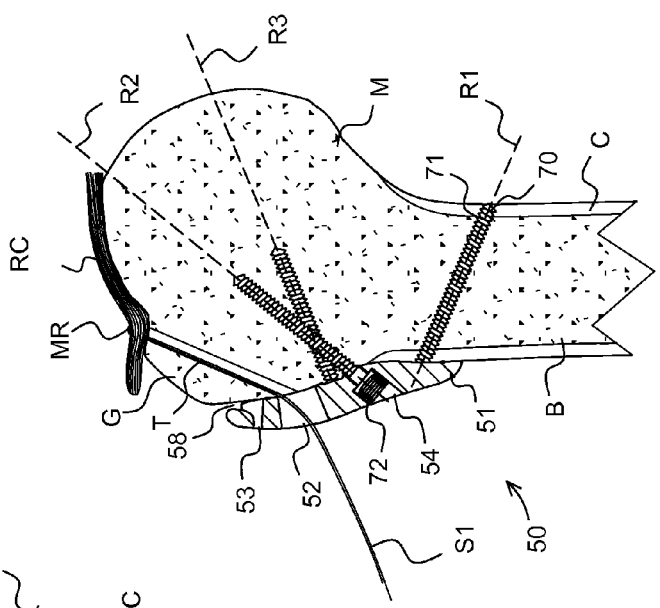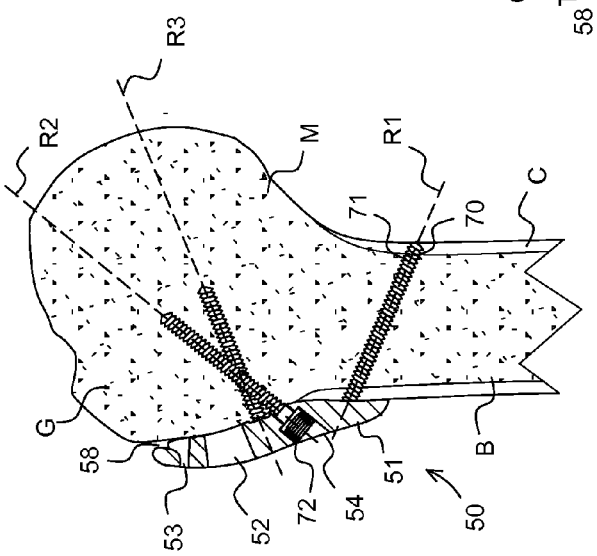

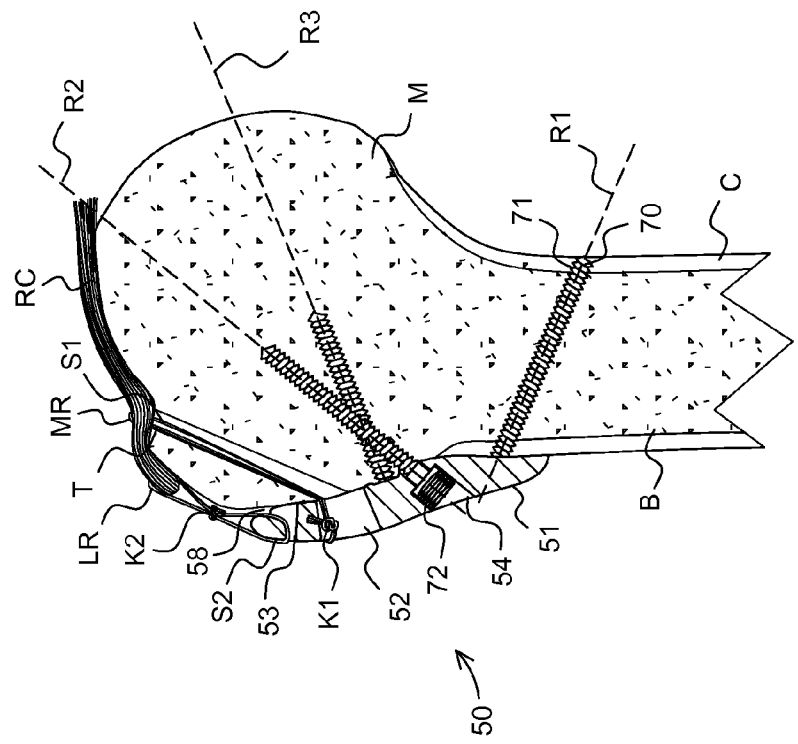
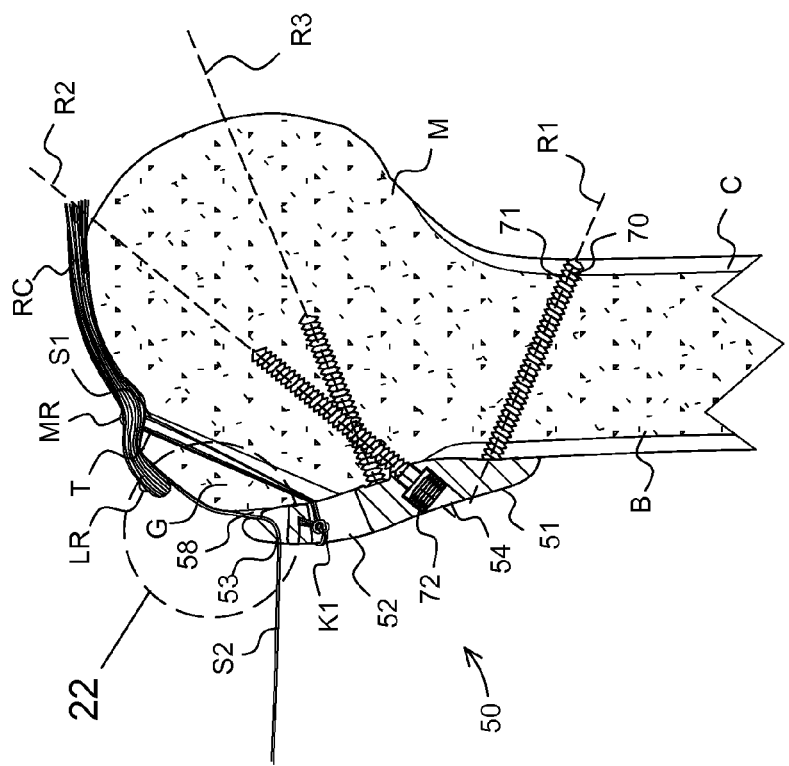

FIXABLE SUTURE ANCHOR PLATE AND METHOD FOR TENDON-TO-BONE REPAIR

BACKGROUND OF THE INVENTION

1. Field of the Invention

The present invention relates to a device and method for anchoring surgical sutures and more specifically to a fixable suture anchor plate and a method for anchoring sutures in a tendon-to-bone repair.

2. Background

When soft tissue tears away from bone, for instance in a rotator cuff tear, reattachment becomes necessary. Various devices, including sutures alone, screws, staples, wedges, plugs and plates have been used to secure soft tissue to bone.

The "rotator cuff" is a group of four muscles, the teres minor, the infraspinatus, the supraspinatus and the subscapularis which work in conjunction to maintain the location of the humerus with respect to the scapula. The muscles of the rotator cuff attach to the scapula and their respective tendons attach to the tuberosities of the humerus forming a cuff. The attachment of these tendons around the humeral head permits the rotator cuff muscles to rotate the humerus. The rotator cuff muscles also oppose and balance against the forces of the deltoid and pectoralis muscles.

Studies indicate that the attachment site between tendon and bone is the weak link during the early healing period, and objective evaluation of rotator cuff repairs shows an approximate 30% rate of failure of secure healing between tendon and bone at 3 to 5 years postoperatively. Clinical studies establish the high rate of residual defects in surgically repaired rotator cuffs and therefore the need to improve devices and methods for these repairs.

When repairing a rotator cuff tendon to bone, one of two methods are most often used: 1) the bone-tunnel method, or 2) the suture-anchor method. Each of the two methods has its relative advantages and disadvantages, and neither can be considered ideal.

The bone-tunnel method involves using a sharp instrument, usually a drill, needle or awl, to create an entry hole near the site of tendon attachment, and an exit hole some distance from the tendon. Surgical sutures are sewn through the tendon, and the free ends of the sutures are then passed through the bone tunnels. Usually multiple bone tunnels are created, and multiple sutures are passed through these tunnels. The free ends of the sutures are then tied over the bone between the bone tunnel exit holes to secure the tendon to the bone. An advantage of the bone-tunnel method is that there is no foreign material left in the patient other than suture. One advantage of the bone-tunnel method as compared with suture anchor repair is that the method may result in superior tendon fixation.

A disadvantage of the bone-tunnel method in a rotator cuff repair is found in its adaptation and use in connection with the relative weak region of bone that is most convenient for tunneling, the lateral metaphyseal bone of the proximal humerus. The sutures used to repair the rotator cuff tendon may actually cut through the soft bone in this region, leading to failure of the tendon-to-bone repair. Devices that are designed to augment the lateral metaphyseal bone of the proximal humerus are held in position simply by the suture that is used for the tendon-to-bone repair. If the sutures were to break, or if the tendon repair were to fail, the hardware would be free to migrate, possibly leading to undesirable consequences.

The second method, the suture-anchor method, involves the use of a suture anchor, which is a screw-like device having an eyelet on one end through which surgical suture may be passed. The suture anchor is inserted through a small hole and screwed deep into the bone. The suture ends are used for securing the tendon to bone.

One advantage of the suture-anchor method is that the tendon-to-bone repair may be performed arthroscopically through a few small skin incisions. The bone-tunnel method requires a larger incision. While arthroscopic repair with suture anchors of smaller rotator tears has been shown to be successful, arthroscopic repairs of larger tears are more prone to failure.

While the use of suture anchors might provide more stable fixation than bone tunnels in some cases, the pull-out strength is still dependent upon the quality of the bone into which the suture anchor is inserted. One of the regions of bone that is most convenient for fixation, the lateral metaphyseal bone of the proximal humerus, is relatively weak. Suture anchors placed in this region are also more prone to pull out of the bone, leading to repair failure. Complications from suture anchor pull-outs range from discomfort to severe joint destruction. While the use of suture anchors has been touted as providing stronger fixation than that of the bone-tunnel method, this claim is debatable. Using suture anchors, the rate of rotator cuff repair failure is still substantial, especially for older patients whose quality of tendon and bone deteriorates with age.

Regardless of whether the bone-tunnel or the suture-anchor method is used, most surgeons feel that is important to optimize the blood supply of the tendon that is to be repaired. The blood supply to the rotator cuff is thought to come from two sources: 1) the bone to which it is attached, and 2) the bursa tissue that overlies the tendon. Due to the inflammatory state that is often associated with injury, the bursa tissue is often abnormal and therefore removed during shoulder surgery. This leaves the bone as the lone remaining blood supply. Though many of the details of the healing process are incompletely understood at this time, many surgeons feel that exposing the tendon to the blood and stem cells that are present in bone marrow likely contributes to successful tendon-to-bone healing. To stimulate such bleeding, the surgeon usually scrapes, drills, or otherwise removes part of the outer layer of bone in the region where the tendon will be reattached. This process is known as decorticating. The disadvantage of this process is that decorticating the bone also weakens it, making suture anchors more likely to come loose and bone tunnels more likely to fail.

Failure of tendon-to-bone repairs may also be attributable to tearing of the tendon by the sutures. Tearing may be reduced when the surgeon employs a suture method whereby a suture is passed through the tendon multiple times in opposing directions rather than with a single pass. When a suture is placed through a tendon with a single pass the suture tends to tear through the tendon much more easily than if the load is distributed by passing the suture through the tendon multiple times in opposing directions. This suture method is much more difficult to achieve when attempted arthroscopically than it is through an open incision, which is why some surgeons prefer to repair the rotator cuff through an open incision rather than arthroscopically.

There is a growing consensus that the ideal method of fixation of the soft tissue to bone would restore the surface area of the pre-injury interface between the soft tissue repair and the bone, recreating what is known as the tendon "footprint." The footprint is defined as the surface area of bone onto which the tendon connects in a nonpathological state (e.g.

before an injury). After surgical repair tendon fibers grow into the bone during the healing period. Having this ingrowth occur over the large surface area that makes up the footprint will lead to a stronger repair as healing occurs.

Suture anchors have been used by some surgeons to achieve a repair that is meant to aid in the restoration of the tendon footprint. According to this method, one or more suture anchors are fixed at the most medial aspect of the greater tuberosity next to the articular surface, and a second anchor or row of anchors is fixed lateral to the greater tuberosity. Sutures are tied across the row of suture anchors fixed at the most medial aspect of the greater tuberosity, and are then "bridged" over the tendon to the second row of anchors. This arrangement holds the tendon against the bone at a medial aspect of the footprint and at a lateral aspect of the footprint. In addition to restoration of tendon-to-bone contact across the footprint, another factor that may contribute to the higher success rates of this method compared to older methods is that the synovial joint fluid is prevented from entering the area of healing. Synovial joint fluid is felt by many to interfere with tendon-to-bone healing.

A need exists to provide a method and apparatus that optimizes tendon-to-bone interface while minimizing motion of the tendon relative to the bone at the interface of the tendon-to-bone repair. Similarly, a need exists to provide a method and apparatus that improves the restoration of the "footprint" of the pre-injury interface between the soft tissue and the bone in a tendon-to-bone repair. There is also a need to provide a method and apparatus that securely attaches the tendon to the bone so that flow of synovial fluid into the surface area of the footprint of the tendon-to-bone repair is minimized. A need also exists to provide a method and apparatus for tendon-to-bone repair that is specifically designed to account for the anatomy of the rotator cuff, proximal humeral bony anatomy and contour, and vascular supply of the humeral head. A need also exists for a method and apparatus for tendon-to-bone repair that allows for decortication of the bone in the area of tendon attachment in order to create an improved blood supply for the healing tendon. The apparatus should allow for strong fixation of the tendon to the bone despite the weakening of the bone that is associated with decortication.

A need also exists to provide a method and apparatus for tendon-to-bone repair that augments the proximal lateral humeral bone to prevent cutting through of the sutures that is secured to the bone with screws. Having the apparatus secured to the bone with screws minimizes the chances that the device would loosen, migrate, and cause injury to the patient. The apparatus should allow for improved fixation during tendon-to-bone repair, especially in soft bone. A need also exists for a method and apparatus that will prevent synovial joint fluid from entering the space between the tendon and bone at the repair site. In addition, a need exists for a device that minimizes the prominence of the knots that are created when surgical sutures are tied during tendon-to-bone repair. Finally, a need exists for a method and apparatus for tendon-to-bone repair that permits passage of a surgical suture and needle through the device after the device is secured to the bone.

Therefore an object of the present invention is to provide a method and apparatus for rotator cuff repair which will reduce or eliminate pull-out of sutures relative to the humerus. Another object of the present invention is to provide a method and apparatus for tendon-to-bone repair which will reduce or eliminate cutting of bone tissue by the sutures and distributes suture forces over a large area both at the bone surface and at the rotator cuff surface. Another object of the present invention is to provide a method and apparatus that increases contact forces at the tendon-to-bone interface while minimizing motion of the tendon relative to the bone at the interface of the tendon-to-bone repair. Similarly, another object of the present invention is to provide a "double-row repair" method and apparatus that improves the restoration of the "footprint" of the pre-injury interface between the soft tissue and the bone in a tendon-to-bone repair. It is a further object of the present invention to provide a method and apparatus for tendon-to-bone repair that is specifically designed to account for the anatomy of the rotator cuff, proximal humeral bony anatomy and contour, and vascular supply of the humeral head.

Additionally, an object of the invention is to provide a method and apparatus that minimizes the prominence of knots created when surgical sutures are tied during tendon-to-bone repair. Another object of the invention is to provide a method and apparatus that will provide strong tendon-to-bone fixation while still allowing the surgeon to decorticate the bone in the region that the tendon is to be attached in order to create a good blood supply for the healing tendon. Another object of the invention is to provide a method and apparatus that will prevent synovial joint fluid from entering the space between the tendon and bone at the repair site. Yet another object of the present invention is to provide a method and apparatus for tendon-to-bone repair that permits passage of a surgical suture and needle through the device after the device is secured to the bone.

SUMMARY OF THE INVENTION

Accordingly, the present invention is directed to a fixable suture anchor plate and a method for tendon-to-bone repair that provides for sewing a first suture along a medial line of tendon attachment forming a medial row of stitches, passing the first suture through a bone tunnel and securing the first suture to the anchor plate and sewing a second suture along a lateral line of tendon attachment forming a lateral row of stitches and securing the second suture to the anchor plate. Alternately, multiple rows of stitches may be employed, sewing each successive suture along a line of tendon attachment and securing the suture to the anchor plate.

More particularly, a fixable suture anchor plate according the present invention is configured as an anchor plate having a medial face and a generally opposing lateral face. The anchor plate includes one or more screw holes adapted to accept the passage of a screw for fixing the anchor plate to the bone. Preferably, there are a plurality of screw holes, each of the screw holes drilled on a unique axis and each of the screw holes adapted to accept a screw having a first thread adapted to threadedly engage the bone fixing the anchor plate to the bone and a second thread adapted to threadedly engage the anchor plate.

In order to accommodate the passage of sutures and needles underneath the anchor plate after the anchor plate is secured to the bone, the anchor plate features a relatively concave medial face having an edge. A section of the edge of the concave medial face includes a notched section characterized by a plurality of grooves. Each of the plurality of grooves terminates at one of the plurality of suture passages formed through the anchor plate. The anchor plate also includes one or more tunnel apertures adapted to communicate with one or more bone tunnels formed in a bone.

In use, each of the pair of tunnel apertures are aligned with a corresponding bone tunnel that passes through the proximal humerus to an entry hole near the site of tendon attachment. Sutures are sewn through the tendon along a medial line of attachment and the free ends of the sutures are passed through the bone tunnels exiting at a corresponding tunnel aperture. One or more sutures are passed through each of the bone tunnels and the free ends of the sutures are tied in such a manner that the sutures pass over a bridge portion of the anchor plate. Preferably, all knots are formed below the lateral face of the anchor plate within the tunnel aperture. In the preferred embodiment of the invention, the periphery of the anchor plate forms an arc having dimension and configuration that is proportional to a contour of the lateral-most insertion site of the supraspinatus, infraspinatus, and teres minor tendons to facilitate suture placement for rotator cuff repair while minimizing the prominence of knots in the tied surgical suture.

The present invention is also directed to a method for tendon-to-bone repair that includes the steps of fixing an anchor plate to the bone at a location proximate to the tendon-to-bone repair, the anchor plate having a plurality of tunnel apertures and a plurality of suture passages. A plurality of bone tunnels are formed in the bone extending from an entry hole located proximate to a medial line of tendon attachment, and an exit hole that communicates with one of the plurality of tunnel apertures.

A first suture is sewn through a tendon that is to be reattached to the bone. The first suture is sewn through the tendon to form a medial row of stitches across the tendon proximate to a medial line of tendon attachment. Free ends of the suture are passed through one of the bone tunnels and its communicating tunnel aperture. The suture free ends are pulled tight drawing the tendon against the bone along the medial row of stitches. The free ends of the suture are secured in such a way as to produce a tensive force between the anchor plate and the medial row of stitches.

A second suture is sewn through the tendon along a line lateral to the medial row of stitches forming a lateral row of stitches. A free end of the second suture is passed through one of the plurality of suture passages. The suture free ends are pulled tight drawing the lateral edge of the tendon against the bone proximate to the lateral row of stitches. The free ends are secured in such a way as to produce a tensive force between the anchor plate and the lateral row of stitches. Because the device and method of the present invention employs bone tunnels, the interface motion of the tendon relative to the bone is improved. Additionally, the device and method of the present invention allow the rotator cuff "footprint" to be restored more effectively by using both a medial and a lateral row of sutures. The location where conventional suture anchors are inserted needs to be decorticated in order to create a new blood supply for the tendon. Decortication tends to further weaken the bone at the site of suture anchor insertion. Advantageously, because fixation of the device is achieved by screws that are distal to the tuberosity, the device and method of the present invention allow the surgeon to decorticate the bone in the region of tendon repair to reestablish healthy blood supply to the tendon without compromising the strength of the repair.

DESCRIPTION OF THE DRAWINGS

FIG. 8 is a representative perspective view of a fixable suture anchor plate according to the present invention;

FIG. 9 is a representative front view of a fixable suture anchor plate according to the present invention;

FIG. 10 is a representative first edge view of a fixable suture anchor plate according to the present invention;

FIG. 11 is a representative back view of a fixable suture anchor plate according to the present invention;

FIG. 12 is a representative second edge view of a fixable suture anchor plate according to the present invention;

FIG. 13 is representative top view of a fixable suture anchor plate according to the present invention;

FIG. 14 is a representative bottom view of a fixable suture anchor plate according to the present invention;

FIG. 17 is a representative perspective view of a fixable suture anchor plate fixed to a bone according to the present invention;

FIG. 18 is a representative perspective view of a fixable suture anchor plate fixed to a bone according to the present invention;

FIG. 19 is a representative perspective view of a fixable suture anchor plate fixed to a bone according to the present invention;

FIG. 20 is a representative perspective view of a fixable suture anchor plate fixed to a bone according to the present invention;

FIG. 21 is a representative perspective view of a fixable suture anchor plate fixed to a bone according to the present invention;

DETAILED DESCRIPTION

Figure 1:
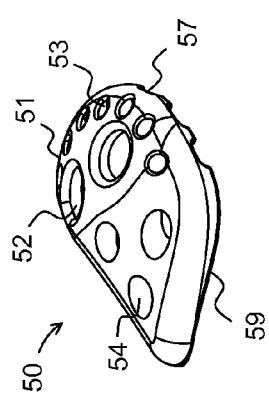
FIG. 1 is a representative perspective view of a fixable suture anchor plate according to the present invention.
Figure 6:
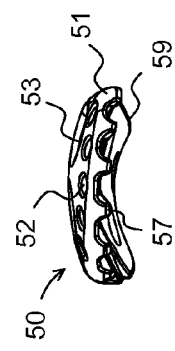
FIG. 6 is representative top view of a fixable suture anchor plate according to the present invention.
Figure 2:
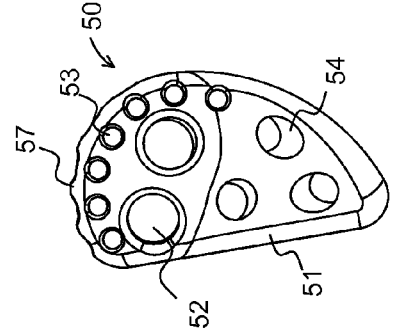
FIG. 2 is a representative front view of a fixable suture anchor plate according to the present invention.
Figure 3:
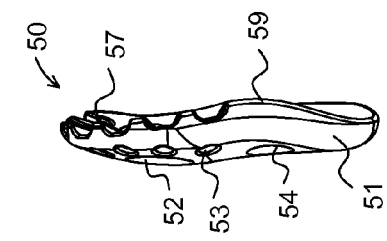
FIG. 3 is a representative first edge view of a fixable suture anchor plate according to the present invention.
Figure 4:
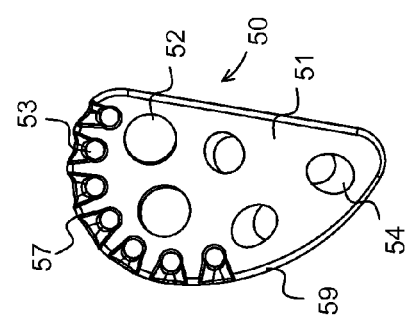
FIG. 4 is a representative back view of a fixable suture anchor plate according to the present invention.
Figure 5:
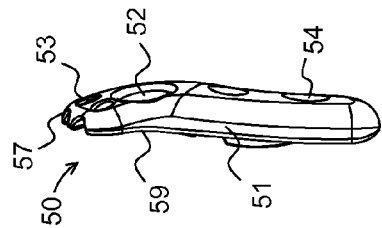
FIG. 5 is a representative second edge view of a fixable suture anchor plate according to the present invention.
Figure 7:
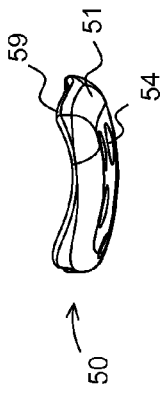
FIG. 7 is a representative bottom view of a fixable suture anchor plate according to the present invention.

Referring to FIGS. 1 through 7 views of fixable suture anchor plate 50 are shown to advantage. Fixable suture anchor plate 50 includes anchor plate 51 having formed therethrough a pair of tunnel apertures typified by tunnel aperture 52 which are adapted for alignment with a bone tunnel formed in a bone, (not shown). Fixable suture anchor plate 50 is configured for use with bone tunnels formed having a relatively large diameter typical of bone tunnels formed with an awl or drill of suitable diameter. Anchor plate 51 also includes a plurality of suture passages typified by suture passage 53 and which are located about a portion of the periphery of anchor plate 51. Three screw apertures typified by screw aperture 54 are adapted to accept screws, (not shown), for fixing anchor plate 51 to a bone, (not shown). Anchor plate 51 also includes edge 59, (FIGS. 1 and 3 through 7), and notched section 57 formed in the periphery defined by edge 59, (FIGS. 1 through 6).

FIGS. 8 through 14 are views showing fixable suture anchor plate 150 to advantage. Fixable suture anchor plate 150 includes anchor plate 151 having formed there-through a plurality of tunnel apertures typified by tunnel aperture 152 which are adapted for alignment with a bone tunnel formed in a bone, (not shown). Fixable suture anchor plate 150 is configured for use with bone tunnels formed having a relatively smaller diameter typical of bone tunnels formed with a needle or a drill of suitable diameter. Anchor plate 151 also includes a plurality of suture passages typified by suture passage 153 and which are located about a portion of the periphery of anchor plate 151. Three screw apertures typified by screw aperture 154 are adapted to accept screws, (not shown), for fixing anchor plate 151 to a bone, (not shown). Anchor plate 151 also includes edge 159, (FIGS. 8 and 10 through 14), and notched section 157 formed in the periphery defined by edge 159, (FIGS. 8 through 13).

FIGS. 1 through 7 and 8 through 14 depict "left hand" versions of fixable suture anchor plates 50 and 150 adapted for a rotator cuff repair for a left arm. The version of either fixable suture anchor plate 50 or fixable suture anchor plate 150 is configured for use in the repair of a rotator cuff attaching to the left arm. A fixable suture anchor plate according to the present invention for use in the repair of a rotator cuff attaching to the right arm would be the mirror image of the "left hand" version.

Figure 16:
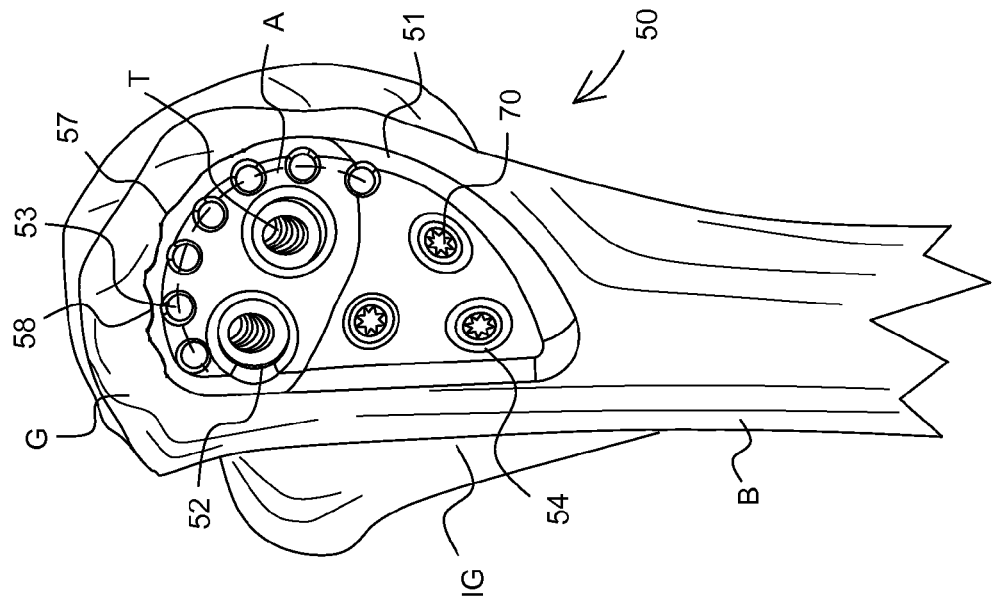
FIG. 16 is a representative perspective view of a fixable suture anchor plate according to the present invention.
Figure 15:
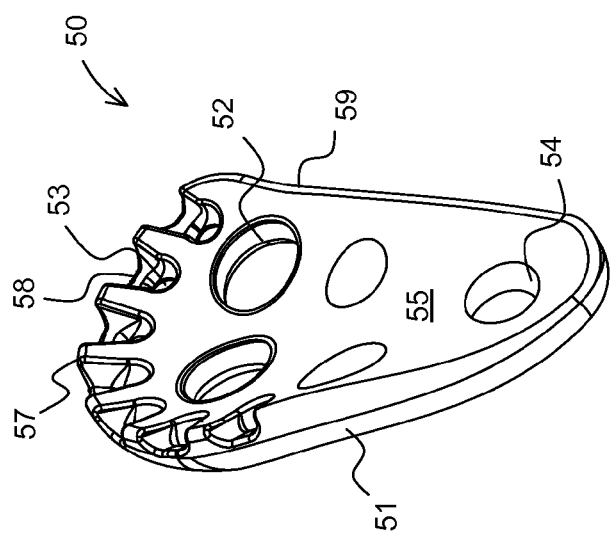
FIG. 15 is a representative perspective view of a fixable suture anchor plate fixed to a bone according to the present invention.

FIG. 15 shows anchor plate 51 including a pair of tunnel apertures typified by tunnel aperture 52, a plurality of suture passages typified by suture passage 53 and three screw apertures typified by screw aperture 54. FIG. 16 shows anchor plate 51 of fixable suture anchor plate 50 including concave medial face 55 having edge 59 having an undulated configuration. Concave medial face 55 and edge 59 are contoured to follow, fit or emulate the proximal humeral bony anatomy and contour. Edge 59 includes notched section 57 having a plurality of grooves typified by groove 58 formed therein, groove 58 communicating with suture passage 53. When anchor plate 51 is secured against a bone, (not shown), the passage of needles and sutures, (not shown), is made possible by the configuration of groove 58 and a communicating suture passage 53. As shown in FIG. 15, all surfaces and edges of tunnel aperture 52, suture passage 53 and groove 58 against which a suture, (not shown), would be pulled across or bear upon.

FIG. 16 shows fixable suture anchor plate 50 including anchor plate 51 attached to humerus bone B. Anchor plate 51 is secured to the greater tubercle G by a plurality of screws typified by screw 70 that insert through a plurality of screw apertures typified by screw aperture 54 threadedly engaging bone B. A pair of tunnel apertures typified by tunnel aperture 52, communicate with two or more tunnels typified by bone tunnel T. Anchor plate 51 also includes a plurality of suture passages typified by suture passage 53, each of the suture passages communicating with one of the plurality of grooves of notched section 57, typified by groove 58, formed along edge 59 of anchor plate 51. The plurality of suture passages typified by suture passage 53 are formed along an arc A, and when fixed to the humerus bone B, anchor plate 51 is oriented such that arc A approximates the curvature of an upper edge of the greater tubercle G providing a number of anchor points for attachment of the "rotator cuff". The generally "D" shaped peripheral configuration of anchor plate 51 is designed to follow the contour of the intertubercular groove IG and the proximal lateral portion of humerus bone B of the left humerus bone. More particularly, the generally "D" shaped peripheral configuration of anchor plate 51 is configured to accommodate the arcuate artery that branches from the anterior humeral circumflex artery, (not shown), and runs superiorly just lateral to the intertubercular groove. A fixable suture anchor plate according to the present invention for use in the repair of a rotator cuff attaching to the right arm would be the mirror image of the "left hand" version or a reverse "D" shaped peripheral configuration.

FIGS. 17 through 21 are a series of representative cutaway figures depicting attachment and use of fixable suture anchor plate 50. Anchor plate 51 is secured generally to the metaphysis M of a long bone and more particularly as shown in FIGS. 17 through 21, to the proximal lateral humeral bone B and its greater tubercle G by three screws typified by screw 70 inserted through a plurality of threaded screw apertures typified by threaded screw aperture 54 threadedly engaging bone B and anchor plate 51, each screw having a distinct and diverging axis of rotation R1, R2 and R3. Screw 70 having axis of rotation R1 extending diagonally down and through humerus bone engaging cortex C. A pair of tunnel apertures typified by tunnel aperture 52, communicate with two or more tunnels typified by bone tunnel T. Anchor plate 51 also includes a plurality of suture passages typified by suture passage 53, each of the suture passages communicating with one of the plurality of grooves, typified by groove 58, formed along notched section 57 of anchor plate 51. Screw 70 includes a first self-tapping thread 71 that is adapted for penetration and fixation with respect to bone B. Screw 70 also includes second thread 72 that is adapted for locking threaded engagement with threaded screw aperture 54. Each threaded screw aperture 54 is configured to threadedly engage second thread 72, locking second thread 72 with respect to threaded screw aperture 54 and anchor plate 51. The locking plate technology provides a fixable suture anchor plate 50 having pullout strength that is far superior to that of suture anchors. Once the screws are locked with respect to the anchor plate, the screws and the anchor plate act as a single fixed-angle device. The screws each having their own axis, with each axis divergent from the others, the plate cannot be pulled away from the bone without completely destroying the bone. Employing this locking plate attachment means, anchor plate 51 is not compressed tightly against bone B, rather it is held at a selected distance from or with a selected compressive force against bone B. Concave medial face 55, shown in FIG. 15, of anchor plate 51 reduces damage to periosteal blood vessels of bone B.

Referring to FIG. 18 bone tunnel is formed through greater tubercle G exiting at one end at tunnel aperture 52. In FIG. 19, first suture S1 has been sewn through rotator cuff RC and is passed through bone tunnel T and tunnel aperture 52. This process is repeated as required by the parameters of a particular repair thereby forming medial row MR of stitching. Referring to FIG. 20 it will be seen that stitching of medial row MR of stitching has been completed proximate to a medial line of attachment of rotator cuff RC, suture S1 has been pulled tight and secured with knot K1. Suture S2 is passed through the end of rotator cuff RC, groove 58 and suture passage 53. Again this process is repeated as required by the parameters of a particular repair thereby forming lateral row LR of stitching. Referring to FIG. 21 it will be seen that stitching of lateral row LR of stitching is complete, suture S2 has been pulled tight and secured with knot K2. In an alternate methodology, successive lateral rows of stitches may be employed, sewing each successive suture along a line of tendon attachment and securing the suture to anchor plate 51.

Figure 22:
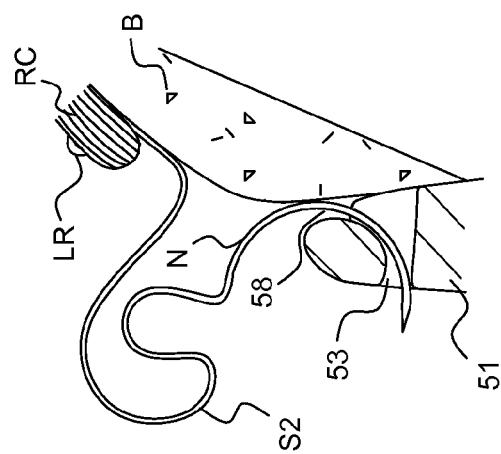
FIG. 22 is a representative detail view of a fixable suture anchor plate according to the present invention.

FIG. 22 is a representative detail showing features of anchor plate 51 that facilitate the passage of a needle N and suture S2 through groove 58 and its communicating suture passage 53. As shown, anchor plate 51 is positioned against bone B. When anchor plate 51 is secured against bone B, the passage of needle N and suture S2 is facilitated by the configuration of groove 58 and the communicating suture passage 53.

Figure 23:
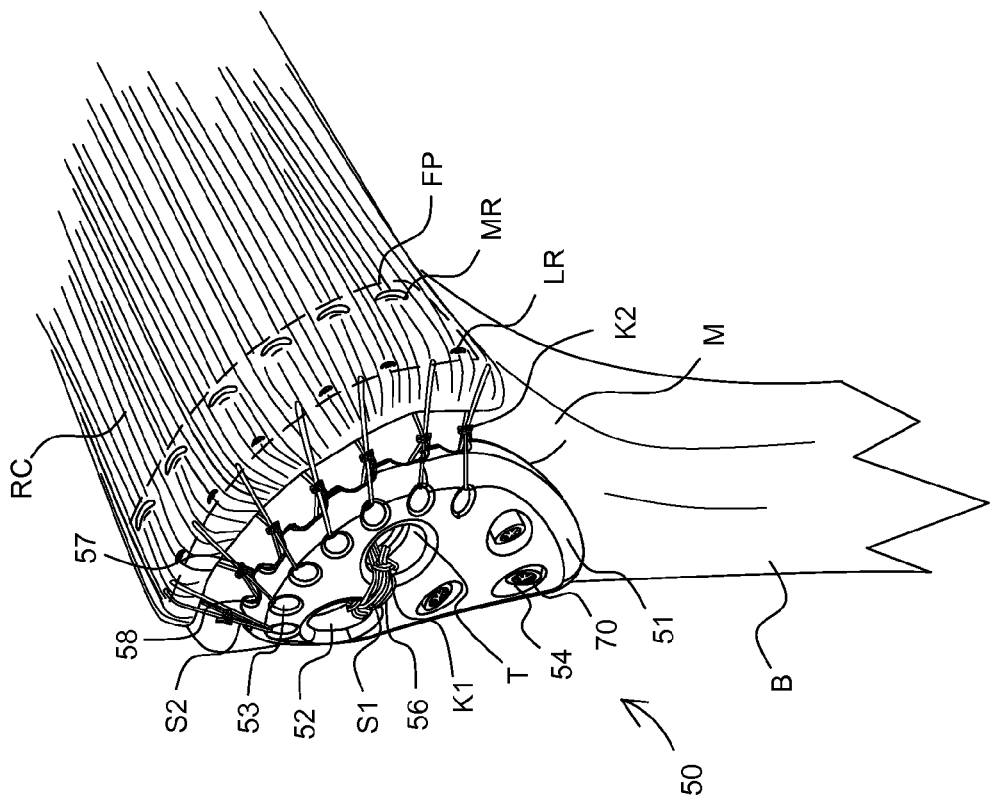
FIG. 23 is a representative perspective view of a fixable suture anchor plate fixed to a bone according to the present invention.

FIG. 23 shows fixable suture anchor plate 50 including anchor plate 51 attached to humerus bone B. Anchor plate 51 is secured by a plurality of screws typified by screw 70 that insert through a plurality of screw apertures typified by screw aperture 54 threadedly engaging bone B. Anchor plate 51 includes a pair of tunnel apertures typified by tunnel aperture 52. Anchor plate 51 also includes a plurality of suture passages typified by suture passage 53, each of the suture passages communicating with one of the plurality of grooves, typified by groove 58, formed along notched section 57 of anchor plate 51.

FIG. 23 shows first suture S1 sewn through rotator cuff RC and passed through bone tunnel T and tunnel aperture 52. This process is repeated as required by the parameters of a particular repair thereby forming medial row MR of stitching located proximate to a medial line of tendon attachment. Sewing of one or more sutures that form medial row MR of stitching has been completed and, suture S1 has been pulled tight and secured with knot K1 across bridge portion 56 that spans between a pair of tunnel apertures typified by tunnel aperture 52. Knot K1 is tied below the surface of bridge portion 56 and within tunnel aperture 52 to minimize the prominence of knot K1 which may relieve patient discomfort. Suture S2 is passed through the end of rotator cuff RC, groove 58 and suture passage 53 pulled tight and secured with knot K2. Again this process is repeated as required by the parameters of a particular repair thereby forming lateral row LR of stitching. FIG. 23 shows footprint FP, indicated by the dashed line, where rotator cuff RC is fixed to bone B by medial row MR of stitching along a medial insertion of rotator cuff RC and lateral row LR of stitching made along a lateral most insertion of rotator cuff RC. Employing fixable suture anchor plate 50 and the method for tendon-to-bone repair herein described improves distribution of suture forces over a larger area both at the tendon-to-bone interface and at the area of attachment of the suture to the bone via fixable suture anchor plate 50. Movement of rotator cuff RC tissue under footprint FP between medial row MR of stitching and lateral row LR of stitching, with respect to bone B is minimized providing a stable and uninterrupted repair that will heal more satisfactorily.

Figure 24:
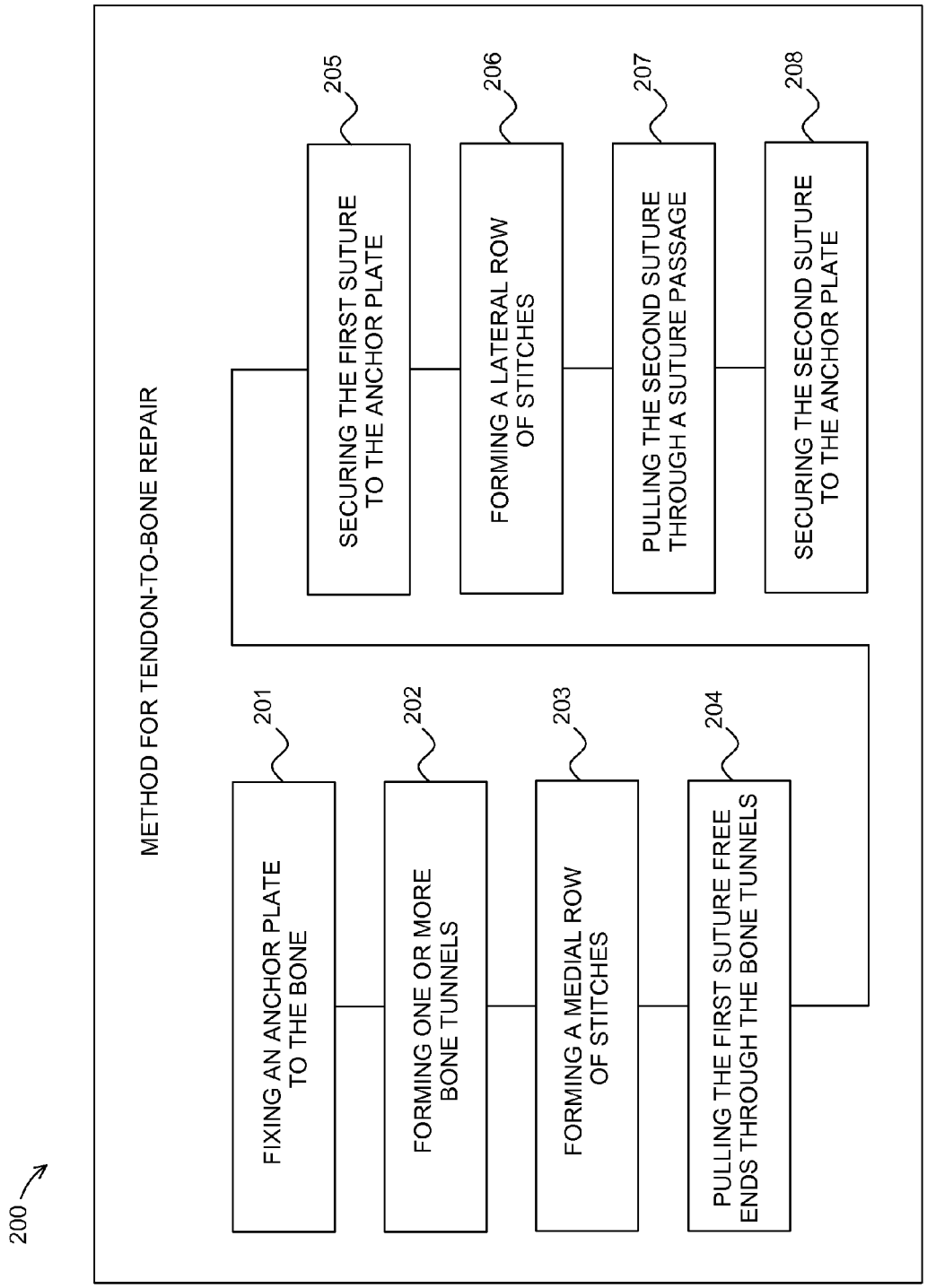
FIG. 24 is a schematic diagram showing steps included in a method according to the present invention.

FIG. 24 is a schematic flow diagram showing the steps of a method for rotator cuff repair using a fixable suture anchor plate according to the present invention. METHOD FOR TENDON-TO-BONE REPAIR 200 includes the steps of FIXING AN ANCHOR PLATE TO THE BONE 201, FORMING ONE OR MORE BONE TUNNELS 202, FORMING A MEDIAL ROW OF STITCHES 203, PULLING THE FIRST SUTURE FREE ENDS THROUGH THE BONE TUNNELS 204, SECURING THE FIRST SUTURE TO THE ANCHOR PLATE 205, FORMING A LATERAL ROW OF STITCHES 206, PULLING THE SECOND SUTURE THROUGH A SUTURE PASSAGE 207 and SECURING THE SECOND SUTURE TO THE ANCHOR PLATE 208.

At FIXING AN ANCHOR PLATE TO THE BONE 201, an anchor plate is fixed to the bone at a location proximate to the tendon-to-bone repair. The anchor plate includes one or more tunnel apertures and one or more suture passages.

At FORMING ONE OR MORE BONE TUNNELS 202, one or more bone tunnels are formed in the bone extending from an entry hole located proximate to a medial line of tendon attachment, and an exit hole that communicates with one of the one or more bone tunnel apertures.

At FORMING A MEDIAL ROW OF STITCHES 203, a first suture is sewn through a tendon that is to be reattached to the bone. The first suture is sewn through the tendon to form a medial row of stitches across the tendon proximate to a medial line of tendon attachment.

At PULLING THE FIRST SUTURE FREE ENDS THROUGH THE BONE TUNNELS 204, a first suture free end is passed through one of the one or more bone tunnels and its communicating tunnel aperture and a second suture free end is similarly passed through a second bone tunnel and its communicating tunnel aperture. The first and second suture free ends of the first suture are pulled tight producing a tensive force along the length of the first suture and drawing the tendon against the bone along the medial row of stitches.

At SECURING THE FIRST SUTURE TO THE ANCHOR PLATE 205, the first and second suture free ends of the first suture are secured in such a way as to maintain the tensive force along the length of the first suture between the anchor plate and the medial row of stitches holding the tendon securely against the bone along the medial row of stitches proximate to the medial line of tendon attachment.

At FORMING A LATERAL ROW OF STITCHES 206, a second suture is sewn through the tendon along a line lateral to the medial row of stitches and proximate to a lateral line of tendon attachment forming a lateral row of stitches.

At PULLING THE SECOND SUTURE THROUGH A SUTURE PASSAGE 207, a free end of the second suture is passed through one of the plurality of suture passages and the first and second suture free ends of the second suture are pulled tight producing a tensive force along the length of the second suture and drawing the tendon against the bone along the lateral line of tendon attachment.

At SECURING THE SECOND SUTURE TO THE ANCHOR PLATE 208, the first and second suture free ends of the second suture are secured in such a way as to maintain the tensive force along the length of the second suture between the anchor plate and the lateral row of stitches holding the tendon securely against the bone along the lateral row of stitches proximate to the lateral line of tendon attachment.

The foregoing description of the illustrated embodiments has been presented for purposes of illustration and description. It is not intended to be exhaustive or to limit the invention to the precise form or to exemplary embodiment(s) and implementation(s) disclosed. Numerous modifications and variations will be apparent to practitioners skilled in this art. Elements described might be interchangeable with other elements in order to achieve the same result. At least one preferred embodiment was chosen and described in order to best explain the principles of the invention and a best mode of practical application, thereby to enable others skilled in the art to understand the invention for various embodiments and with various modifications as are suited to the particular use or implementation contemplated. It is intended that the scope of the invention be defined by the claims appended hereto and their equivalents. Reference to an element in the singular is not intended to mean "one and only one" unless explicitly so stated, but rather means "one or more." Moreover, no element, component, nor method step in the present disclosure is intended to be dedicated to the public regardless of whether the element, component, or method step is explicitly recited in the following claims. No claim element herein is to be construed under the provisions of 35 U.S.C. Sec. 112, sixth paragraph unless the element is expressly recited using the phrase "means for . . . "

What is claimed is:

1. A fixable suture anchor plate for a rotator cuff to humerus repair, the humerus including a proximal humeral bony anatomy and contour, the rotator cuff to humerus repair performed with a first suture passed through the rotator cuff and one of a plurality of bone tunnels formed in the humerus for attachment to the fixable suture anchor plate and a second suture passed through the rotator cuff for attachment to the fixable suture anchor plate the fixable suture anchor plate comprising:

an anchor plate comprising a "D" shaped peripheral edge configuration consisting of a single straight peripheral edge portion, joined at a first end to a first end of a single continuously curving peripheral edge portion, the substantially straight peripheral edge portion joined at a second end to a second end of the single curving peripheral edge portion, the anchor plate including a concave medial surface;

a plurality of threaded screw apertures formed in the anchor plate, each of the plurality of threaded screw apertures adapted to accept a screw for fixing the anchor plate with respect to the proximal end of the humerus bone;

a plurality of tunnel apertures formed through the anchor plate, each of the a plurality of tunnel apertures configured to communicate with one of the plurality of bone tunnels to permit passage of the first suture through at least one of the plurality of tunnel apertures;

one or more suture passages formed through the anchor plate, the one or more suture passages located proximate to an upper edge of the anchor plate; and one or more grooves formed on the medial side of the anchor plate along the upper edge of the anchor plate, each of the one or more grooves communicating with at least one of the one or more suture passages, the one or more grooves and one or more suture passages configured to permit passage of the second suture through one of the one or more grooves and a communicating suture passage.

2. The fixable suture anchor plate of claim 1 wherein the one or more suture passages and the one or more grooves are configured to facilitate passage of a needle after the anchor plate is secured to the humerus.

3. The fixable suture anchor plate of claim 1 further comprising a plurality of screws, each of the plurality of screws adapted for passage through one of the plurality of threaded screw apertures for fixing the anchor plate to the humerus.

4. The fixable suture anchor plate of claim 1 wherein each of the plurality of threaded screw apertures further comprise:

an axis, the axis of each of the plurality of threaded screw apertures diverging from the axis of each of the remaining plurality of threaded screw apertures; and a plurality of screws, each of the plurality of screws including a thread adapted for threadedly engaging one of the plurality of threaded screw apertures.

5. A fixable suture anchor plate for a rotator cuff to humerus repair, the humerus including a proximal humeral bony anatomy and contour, a greater tubercle, a proximal lateral portion and an intertubercular groove, the rotator cuff to humerus repair performed with a first suture passed through the rotator cuff and one of a plurality of bone tunnels formed in the humerus for attachment to the fixable suture anchor plate and a second suture passed through the rotator cuff for attachment to the fixable suture anchor plate, the fixable suture anchor plate comprising:

an anchor plate comprising a reverse "D" shaped peripheral edge consisting of a single continuously straight peripheral edge portion, joined at a first end to a first end of a single reverse curving peripheral edge portion, the substantially straight peripheral edge portion joined at a second end to a second end of the single reverse curving peripheral edge portion, the anchor plate including a concave medial surface;

a plurality of threaded screw apertures formed in the anchor plate, each of the plurality of threaded screw apertures adapted to accept a screw for fixing the anchor plate with respect to the proximal end of the humerus;

a plurality of tunnel apertures formed through the anchor plate, each of the plurality of tunnel apertures configured to communicate with one of the plurality of bone tunnels to permit passage of the first suture through one of the plurality of tunnel apertures;

one or more suture passages formed through the anchor plate, the one or more suture passages located proximate to an upper edge of the anchor plate; and one or more grooves formed on the medial side of the anchor plate along the upper edge of the anchor plate, each of the one or more grooves in communication with at least one of the one or more suture passages, the one or more grooves and the one or more suture passages configured to permit passage of the second suture through one of the one or more grooves and a communicating suture passage.

6. The fixable suture anchor plate of claim 5 wherein each of the plurality of threaded screw apertures further comprise:

an axis, the axis of each of the plurality of threaded screw apertures diverging from the axis of each of the remaining plurality of threaded screw apertures; and a plurality of screws, each of the plurality of screws including a thread adapted for threadedly engaging one of the plurality of threaded screw apertures.

7. The fixable suture anchor plate of claim 6 wherein the one or more suture passages and the one or more grooves are configured to permit passage of a needle after the anchor plate is fixed to the humerus.

8. A fixable suture anchor plate system for, a rotator cuff to humerus repair, the humerus including a proximal humeral bony anatomy and contour, the rotator cuff to humerus repair performed with a first suture passed through the rotator cuff and one of a plurality of bone tunnels formed in the humerus for attachment to the fixable suture anchor plate and a second suture passed through the rotator cuff for attachment to the fixable suture anchor plate, the fixable suture anchor plate consisting essentially of:

an anchor plate selected from a group of anchor plates including an anchor plate comprising a "D" shaped peripheral edge configuration consisting of a single continuously straight peripheral edge portion, joined at a first end to a first end of a single curving peripheral edge portion, the substantially straight peripheral edge portion joined at a second end to a second end of the single curving peripheral edge portion, and an anchor plate including a reverse "D" shaped peripheral edge configuration consisting of a single substantially straight peripheral edge portion, joined at a first end to a first end of a single reverse curving peripheral edge portion, the substantially straight peripheral edge portion joined at a second end to a second end of the single reverse curving peripheral edge portion;

a plurality of tunnel apertures formed through the anchor plate, each of the plurality of tunnel apertures configured to communicate with one of the plurality of bone tunnels to permit passage of the first suture through one of the plurality of tunnel apertures;

a plurality of suture passages formed through the anchor plate, the plurality of suture passages located proximate to an upper peripheral edge of the anchor plate;

one or more grooves formed on the medial side of the anchor plate, the one or more grooves formed along the upper peripheral edge of the anchor plate, each of the one or more grooves communicating with at least one of the plurality of suture passages, the one or more grooves and the plurality of communicating suture passages configured to permit passage of the second suture through one of the one or more grooves and a communicating suture passage after the anchor plate is fixed to the bone;

a plurality of threaded apertures formed in the anchor plate, each of the plurality of threaded apertures having an axis, the axis of each of the plurality of threaded apertures diverging from the axis of each of the remaining plurality of threaded apertures.

* * * * *